United States Patent [19]

Gravenstein et al.

[11] Patent Number: 4,702,241
[45] Date of Patent: Oct. 27, 1987

[54] SELF-CONTAINED JET PUMP BREATHING APPARATUS

[75] Inventors: Joachim S. Gravenstein; Samsun Lampotang, both of Gainesville, Fla.

[73] Assignee: University of Florida, Gainesville, Fla.

[21] Appl. No.: 786,468

[22] Filed: Oct. 11, 1985

[51] Int. Cl.$^4$ .............................................. A61M 16/00
[52] U.S. Cl. .......................... 128/204.25; 128/205.12; 128/205.19; 128/910
[58] Field of Search ...................... 128/203.12, 203.25, 128/203.28, 204.18, 204.24, 204.25, 205.12, 205.13, 205.17, 205.19, 205.24, 910

[56] References Cited

U.S. PATENT DOCUMENTS

| | | | |
|---|---|---|---|
| 1,630,501 | 5/1927 | Steese | 128/204.25 |
| 2,325,049 | 7/1943 | Frye et al. | 128/204.25 |
| 2,766,753 | 10/1956 | Koch et al. | 128/205.14 |
| 3,485,243 | 12/1969 | Bird et al. | 128/204.25 |
| 4,007,737 | 2/1977 | Paluch | 128/911 |
| 4,188,946 | 2/1980 | Watson et al. | 128/910 |
| 4,245,633 | 1/1981 | Erceg | 128/205.17 |
| 4,281,652 | 8/1981 | Miller | 128/911 |
| 4,463,756 | 8/1984 | Thuc | 128/204.24 |
| 4,481,944 | 11/1984 | Bunnell | 128/204.18 |
| 4,520,812 | 6/1985 | Freitag et al. | 128/204.25 |
| 4,543,451 | 10/1985 | Phuc | 128/910 |
| 4,573,462 | 3/1986 | Baum | 128/204.25 |

Primary Examiner—Henry J. Recla
Assistant Examiner—Karin M. Reichle
Attorney, Agent, or Firm—Dennis P. Clarke

[57] ABSTRACT

A self-contained jet pump type breathing apparatus is provided for introducing gases into the lungs of a patient having an inspiratory jet pump for sweeping gases toward the patient, an expiratory jet pump for sweeping exhaled gases away from the patient and an absorber for absorbing carbon dioxide from the exhaled gases which are again supplied to the respiratory jet pump. An anesthetic introduction conduit permits the flow of anesthetic gases into the breathing apparatus. In addition, a jet producer device, is also provided, which obtains fresh compressed gases from the absorber and compressor and supplies pulsating pressurized gases to the respiratory jet pumps.

9 Claims, 4 Drawing Figures

SELF-CONTAINED JET PUMP BREATHING APPARATUS

TECHNICAL FIELD

The present invention relates to breathing apparatus for introducing gases to the lungs of a patient and, more particularly, to a self-contained breathing apparatus for introducing gases into the lungs of a patient having inspiratory and expiratory jet pumps for sweeping gases toward and away from the patient minimizing the effect of dead space.

DISCUSSION OF PRIOR ART

Currently there are three types of breathing systems in common use. Breathing systems or apparatus as used throughout the application include breathing systems having devices for introducing anesthetic gases into the lungs of a patient. The three breathing systems are the circle system, valveless systems and high frequency ventilation systems.

The circle system illustrated in FIG. 1 operates as follows. A patient at point 1 inhales fresh gases through inspiratory valve 2 which permits gases to flow in a single direction toward the patient. The patient at point 1 must inhale with sufficient force to open the inspiratory valve 2 in order to receive the fresh gases. Gases exhaled by the patient at point 1 is forced through expiratory valve 3 which permits gases to flow in a single direction away from the patient. The patient at point 1 must exhale with sufficient force to open the expiratory valve 3 in order to move the exhaled gases beyond the expiratory valve 3 for further treatment. An absorber 4 receives the exhaled gases forced through the expiratory valve and removes carbon dioxide produced by the patient thereby producing fresh gases which are inhaled by the patient through the inspiratory valve 1. The circle system suffers from various disadvantages. For example, the valves require some effort to open during inspiration and expiration and are therefore undesirable for use on newborns, infants and others severely weakened by sickness, injury or surgery. Another disadvantage of the circle system resides on the fact that there is a potential for dead space between the inspiratory and expiratory valves. Dead space allows the patient to re-inhale some of the exhaled gases deposited into the system.

As stated above, the second type of breathing system is called the valveless system, namely the Mapleson system of which a modification called the Bain system is shown in FIG. 2. In the Bain system fresh gases are supplied through a central tube 5. A patient at point 6 inhales fresh gases from the central tube 5 and exhales gases into the expiratory tube 8 as shown by the arrow 7. As long as the fresh gas flow rate exceeds the peak inspiratory flow rate of the patient no re-breathing of the exhaled gases takes place. However, when the peak inspiratory flow rate exceeds the flow rate of the fresh gas supplied through the central tube the patient re-inhales some of the exhaled gases deposited into the expiratory tube. Therefore, the Bain system requires a high fresh gas flow rate which must be anticipated for each patient by using a complex formula which is subject to inaccuracies.

The third system, known as a high frequency jet ventilation system, is shown in FIG. 3 and operates as follows. A jet nozzle 9 brought close to the patient's mouth or the patient's endotracheal tube supplies pulsating gases which entrain the air surrounding the jet nozzle thereby, blowing the surrounding air down the patient's trachea. The gases in the jet nozzle are pulsed at a rate to simulate a respiratory rate of at least 100 breaths per minute. The jet nozzle of the high frequency jet ventilation system requires a high fresh gas flow rate which must be anticipated for each patient by using a complex formula which is subject to inaccuracies.

The three systems described above are not interchangeable without extensive and tedious modifications. In addition, the second and third systems described above use large amounts of anesthetic gases when employed to anesthetize the patient.

OBJECTS AND SUMMARY OF THE PRESENT INVENTION

It is therefore an object of the present invention to provide a breathing apparatus that will minimize the effect of dead space.

Another object of the present invention is to provide a breathing apparatus that does not use valves to obtain unidirectional gas flow.

Still another object of the present invention is to provide a breathing apparatus that does not need a high net fresh gas flow rate in order to meet the needs of the patient at peak inspiratory rates.

Yet another object of the present invention is to provide a breathing apparatus that uses less anesthetic vapors and gases than conventional breathing apparatus.

It is yet another object of the present invention to provide a breathing apparatus that meets the patient's metabolic need for oxygen.

A further object of the present invention is to provide a breathing apparatus that offers minimal resistance to inhalation and exhalation.

Still yet another object of the present invention is to provide a breathing apparatus which offers rapid mixing of anesthetic gases with fresh gases.

A still further object of the present invention is to provide a breathing apparatus which allows the user to operate the breathing apparatus either as a circle system, a Bain system or a high frequency jet ventilation system.

In accordance with the above and other objects of the present invention, there is provided a self-contained jet pump breathing apparatus for introducing gases into the lungs of a patient having an inspiratory jet pump for sweeping gases toward the patient, an expiratory jet pump for sweeping exhaled gases away from the patient and an absorber for absorbing carbon dioxide from the exhaled gases producing fresh gases which are again supplied to the jet pumps. An anesthetic introduction conduit permits the flow of anesthetic gases into the breathing apparatus to be inhaled by the patient. In addition, a jet producer device, is also provided, which obtains fresh gases from the absorber and supplies pressurized gases to the jet pumps thereby driving the jet pumps and causing the sweeping of the fresh and exhaled gases.

BRIEF DESCRIPTION OF THE DRAWINGS

The above and still further objects, features and advantages of the present invention will become apparent upon consideration of the following detailed description of specific embodiments thereof, especially, when considered in conjunction with the accompanying drawings wherein like parts in each of the several figures are identified by the same reference numerals, and wherein.

DESCRIPTION OF THE PREFERRED EMBODIMENT

Figure 1:
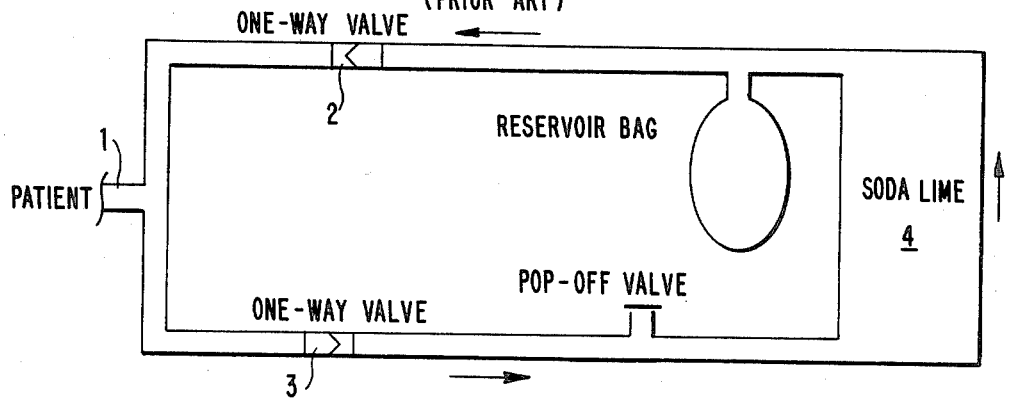
FIG. 1 is a schematic diagram of a prior art circle system.
Figure 2:
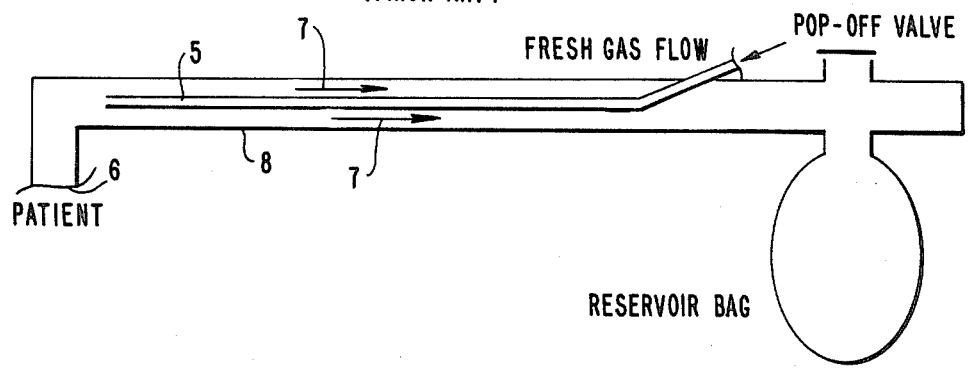
FIG. 2 is a schematic diagram of a prior art valveless Bain system.
Figure 3:
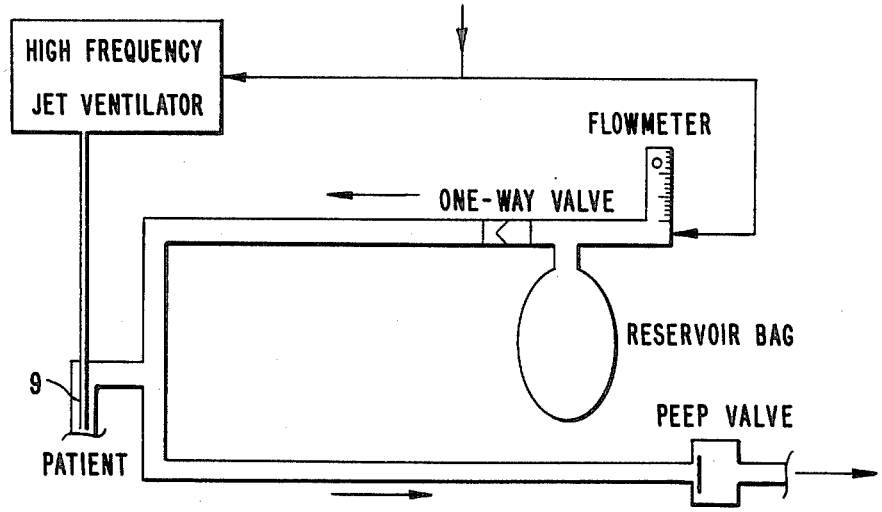
FIG. 3 is a schematic diagram of a prior art high frequency jet ventilation system.

Referring specifically to the schematic diagrams of FIGS. 1, 2 and 3, three conventional systems are shown: a circle system, a Bain system and a high frequency jet ventilation sytem, respectively. The operation of each of the conventional systems are discussed above in the discussion of the prior art which also points out for each system various features and disadvantages. The present invention overcomes all of the disadvantages of the conventional systems to provide a self-contained jet pump breathing apparatus as shown in FIG. 4.

Figure 4:
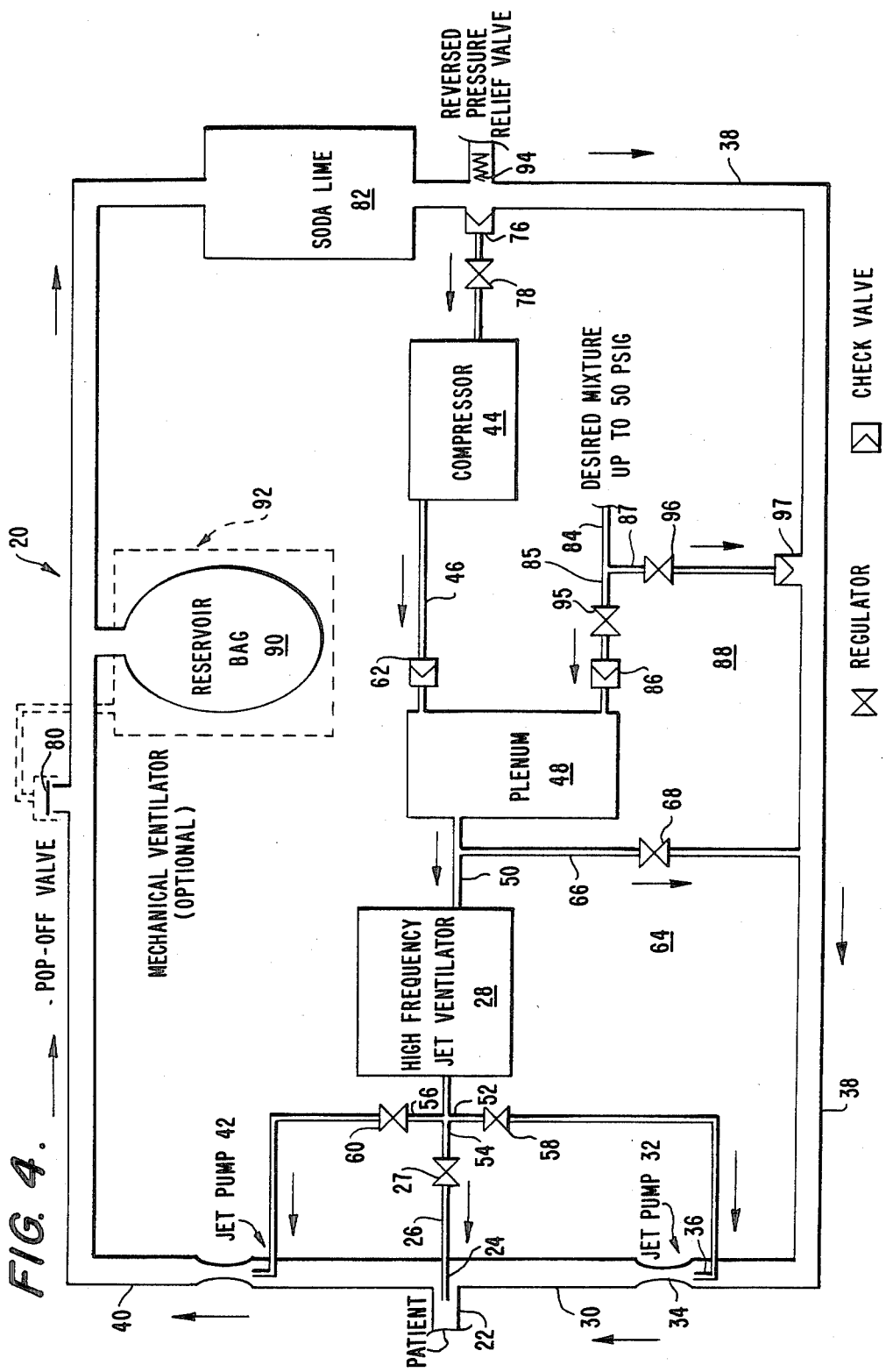
FIG. 4 is a schematic diagram of a self-contained jet pump breathing apparatus in accordance with the present invention.

Referring to FIG. 4 of the drawing, the present invention comprises a gas introduction device generally designated 20. Gas is directed to the patient via outlet 22 provided with an injection jet 24 connected via a conduit 26 with a high frequency jet ventilation unit 28. Air or a mixture of air and oxygen or air, oxygen and anesthetics is directed to the outlet 22 via inhalation circuit pipe 30 provided with a jet pump 32. The jet pump 32 or ejector comprises a venturi section 34 and an injector pipe 36. Air or a mixture of gases is directed to the upstream side of the jet pump 32 via conduit 38. Exhaled gases from the patient are directed into the circuit via conduit 40 by a second jet pump generally designated 42 configured in a manner as the jet pump 32 in the inhalation side of the circuit.

Compressed gas for operating the high frequency jet ventilation unit 28, its jet 24 and jet pumps 32 and 42 is conveyed from a compressor 44, outlet pipe 46 to a plenum 48 which assists in making the output from the compressor more uniform. The outlet pipe 50 from the plenum chamber goes to the high frequency ventilation 28 and is then divided into three branches 52, 54 and 56. Pipe 52 directs air to the ejector pipe 36 of jet pump 32 via a control valve generally designated 58 which regulates the output of the jet pump 32.

Pipe 54 flows to jet 24 while pipe 56 flows via a control valve 60 to the jet pump 42 on the exhalation side of the circuit.

As a safety feature, a one-way valve 62 may be placed in the pipe 46 from the compressor.

As illustrated the compressor 44 may be provided with a bypass circuit generally designated 64. The bypass circuit consists of a pressure pipe 66, a control valve 68 which opens when the pressure in pipe 50 exceeds a preset value. A make-up circuitry generally designated 88 is employed to bring in make-up gas to the plenum 48. Where the make-up gas is not employed, a portion of the gas on the inhalation side of the circuit from pipe 38 is directed via a one-way valve 76 and a variable control valve 78 to the compressor 44. Thus, all of the gas passing through the compressor 44 may be from conduit 38 or all of the gas in the plenum may be from make-up circuit 88 or any combination thereof. Line 38 is also provided with a reversed pressure relief valve 94. The exhalation pipe 40 is provided with a conventional pop-off valve 80 to prevent over pressuring of the system or to bleed excess gases therefrom. Gases in pipe 40 that do not escape through pop-off valve 80 flow through a soda lime $CO_2$ absorption device generally designated 82. The output gases from the soda lime $CO_2$ absorption chamber flow into conduit 38. A make-up circuit 88 and pipe 84 provided with a one-way valve 86 is for injection into the plenum 48 via line 85, regulator 95 and check valve 86 or into the inhalation pipe 38 via line 87, regulator 96 and check valve 97 or both of oxygen, anesthetics, or other gases as the case may be. The system may also be provided with a conventional reservoir bag 90 which permits intermittent positive pressure exerted through the breathing bag. The plenum 88 is also effective to limit pressure fluctuations in the pressurized gases received from the compressor means 44 to a low pressure limit of 50 psig and a high pressure limit of 60 psig.

The high frequency jet ventilation unit 28 is of the adjustable type to provide, for example, 100 breaths/min. or more and is a commercial unit. Satisfactory results have been obtained with Model 300 made by Healthdyne. From the foregoing description of the ventilator 20, FIG. 4 of the drawing, it will be seen that a very versatile system is provided. It is also contemplated that various modifications may be made in the system, for example, a conventional mechanical ventilator 92 shown in broken lines may replace the reservoir or breathing bag 90.

The jet breathing circuit permits operation of the high frequency jet ventilation system in a conventional manner in which it simply entrains fresh gas from the inspiratory tube and vents exhaled gas into the expiratory tube where these gases are swept along by the two circuit jets that assure uni-directional flow.

It will also be recognized that the regulator valves such as 27, 58, 60, 68, 78, 95, and 96 allow adjustment of the gas flow individually through all of the three jets, allow adjustment of the fresh gas flow entering the system, allow the addition of inhalation anesthetics entering the system either through the uni-directional circuit jets or through the high frequency injection jet.

In an experimental prototype the jet pumps 32 and 42 were "Bird Trijets 2587" coupled to a "Bird" 999 2027 Venturi. The compressor comprised an electrically powered 1/6 horsepower SKLAR compressor unit with a flow rate of 5 L/min. through each jet pump nozzle to thereby generate a total circular gas flow of 40 L/min.

What is claimed is:

1. For introducing gases into the lungs of a patient, a self-contained jet pump breathing apparatus comprising:
    gas introduction means for supplying gas to and receiving gas from the lungs of the patient;
    inspiratory conduit means for supplying gas to said gas introduction means;
    expiratory conduit means for receiving gas from said gas introduction means;
    third conduit means for fluidically communicating said inspiratory conduit means with said expiratory conduit means; a conduit loop defined by said inspiratory conduit means, said expiratory conduit means and said third conduit means;
    inspiratory jet pump means operatively positioned in said inspiratory conduit means for sweeping fresh gases toward the gas introduction means;

expiratory jet pump means operatively positioned in said expiratory conduit means for sweeping gases exhaled by the patient away from the gas introduction means;

gas compressor means having an inlet and an outlet, and outlet conduit means connected to the compressor means outlet for supplying compressed gas from the gas compressor means to the inspiratory and expiratory jet pumps and inlet conduit means connected between the compressor means inlet and said conduit loop for supplying gas to said compressor means; and wherein said gas introduction means includes jet nozzle means for receiving compressed gas from the gas compressor means outlet by way of said outlet conduit means to thereby provide gas to the lungs of the patient.

2. The self-contained jet pump breathing apparatus as defined in claim 1, further including a high frequency jet producing means for supplying pulsed jets of the compressed gas to the jet nozzle means.

3. The self-contained jet pump breathing apparatus of claim 1 further including:

plenum means communicating with said gas compressor means for limiting pressure fluctuations in the compressed gases received by the outlet conduit means from the gas compressor means.

4. The self-contained jet pump breathing apparatus of claim 3 further including:

$CO_2$ absorber means operatively positioned in said third conduit means for absorbing carbon dioxide from the gases exhaled by the patient thereby producing rebreathable gases which are supplied to said inspiratory conduit means.

5. The self-contained jet pump breathing apparatus of claim 3 wherein the plenum means limits pressure fluctuations in the compressed gases received from the compressor means to a low pressure limit of 50 psig and a high pressure limit of 60 psig.

6. The self-contained breathing apparatus of claim 5 further comprising:

mechanical ventilator means operatively connected in the expiratory conduit means.

7. The self-contained jet pump breathing apparatus of claim 1 further comprising:

a breathing bag operatively connected in the expiratory conduit means adapted to be manipulated by an examining physician to generate intermittent changes of pressure in the conduit loop.

8. For introducing gases into the lungs of a patient, a self-contained jet pump breathing apparatus comprising:

gas introduction means for supplying gas to and receiving gas from the lungs of the patient;

inspiratory conduit means for supplying gas to said gas introduction means;

expiratory conduit means for receiving gas from said gas introduction means;

third conduit means for fluidically communicating said inspiratory conduit means with said expiratory conduit means; a conduit loop defined by said inspiratory conduit means, said expiratory conduit means and said third conduit means;

inspiratory jet pump means operatively positioned in said inspiratory conduit means for sweeping fresh gases toward the gas introduction means;

expiratory jet pump means operatively positioned in said expiratory conduit means for sweeping gases exhaled by the patient away from the gas introduction means;

gas compressor means having an inlet and an outlet, and outlet conduit means connected to the compressor means outlet for supplying compressed gas from the gas compressor means to the inspiratory and expiratory jet pumps, and inlet conduit means connected between the compressor means inlet and said conduit loop for supplying gas to said compressor means; and said gas introduction means including jet nozzle means for receiving compressed gas from the gas compressor means outlet by way of said outlet conduit means to thereby provide gas to the lungs of the patient;

plenum means communicating with said gas compressor means for limiting pressure fluctuations in the compressed gases received by the conduit means from the compressor means;

$CO_2$ absorber means operatively positioned in said third conduit means for absorbing carbon dioxide from the gases exhaled by the patient thereby producing rebreathable gases which are supplied to said inspiratory conduit means; and further comprising:

anesthetic introduction conduit means for communicating a source of breathing gas with the plenum means and with the inspiratory conduit means.

9. The self-contained jet pump breathing apparatus of claim 8 further including a plurality of gas flow regulators including:

a first gas flow regulator operatively positioned in the outlet conduit means for supplying compressed gas to said inspiratory jet pump means and a second gas flow regulator operatively positioned in the outlet conduit means for supplying compressed gas to said expiratory jet pump means.

* * * * *